US010625070B2

(12) United States Patent
Schlitt et al.

(10) Patent No.: US 10,625,070 B2
(45) Date of Patent: Apr. 21, 2020

(54) CONNECTING DEVICE FOR A MEDICAL INFUSION SYSTEM

(71) Applicant: B. Braun Melsungen AG, Melsungen (DE)

(72) Inventors: Christof Schlitt, Obergrenzebach (DE); Frank Eisen, Escholzmatt (CH); Martin Schneider, Thun (CH); Ralf Kunschak, Willisau (CH); Matthias Denk, Langnau i. E. (CH); Fritz Zwygart, Hasle bei Burgdorf (CH); Mayur Dudhane, Escholzmatt (CH); Samuel Bertschi, Schüpfheim (CH)

(73) Assignee: B. Braun Melsungen AG (DE)

( * ) Notice: Subject to any disclaimer, the term of this patent is extended or adjusted under 35 U.S.C. 154(b) by 344 days.

(21) Appl. No.: 15/446,119

(22) Filed: Mar. 1, 2017

(65) Prior Publication Data
US 2017/0252551 A1 Sep. 7, 2017

(30) Foreign Application Priority Data

Mar. 3, 2016 (DE) .................. 10 2016 203 518

(51) Int. Cl.
*A61M 39/22* (2006.01)
*A61M 39/04* (2006.01)
(Continued)

(52) U.S. Cl.
CPC .......... *A61M 39/22* (2013.01); *A61M 39/045* (2013.01); *A61M 39/10* (2013.01);
(Continued)

(58) Field of Classification Search
CPC .......... A61M 2039/22; A61M 2039/26; A61M 2039/267; A61M 39/22; A61M 39/26;
(Continued)

(56) References Cited

U.S. PATENT DOCUMENTS 1,890,011 A * 12/1932 Wirz ................. F16L 37/248
285/95
5,251,873 A 10/1993 Atkinson et al.
(Continued)

FOREIGN PATENT DOCUMENTS

DE 69317422 T2 7/1998
EP 0748635 A2 12/1996
(Continued)

OTHER PUBLICATIONS

German Search Report for German Application No. 10 2016 203 518.5, dated Sep. 9, 2016 with partial translation—10 Pages.
(Continued)

*Primary Examiner* — Kevin F Murphy
*Assistant Examiner* — Jonathan J. Waddy
(74) *Attorney, Agent, or Firm* — RatnerPrestia

(57) ABSTRACT

A connecting device for a medical infusion system includes a connection piece which has a connecting profile for the connection of a functional part of the infusion system. The connecting device also has a resiliently flexible, cup-like valve body which is arranged in the connection piece and has a valve casing and cap-shaped top region which is provided with a slit arrangement. Further, the connecting device has a dimensionally stable base portion on which a base ring of the valve casing is supported and which is firmly connected to the connection piece. In the unloaded initial state, the valve casing has a convex internal contour which, starting from the cap-shaped top region, first expands in the direction of the base ring and subsequently narrows again, forming an O-like internal longitudinal section. The connecting device can be in the form of a three-way stopcock for an infusion system.

11 Claims, 5 Drawing Sheets

Figure 1:
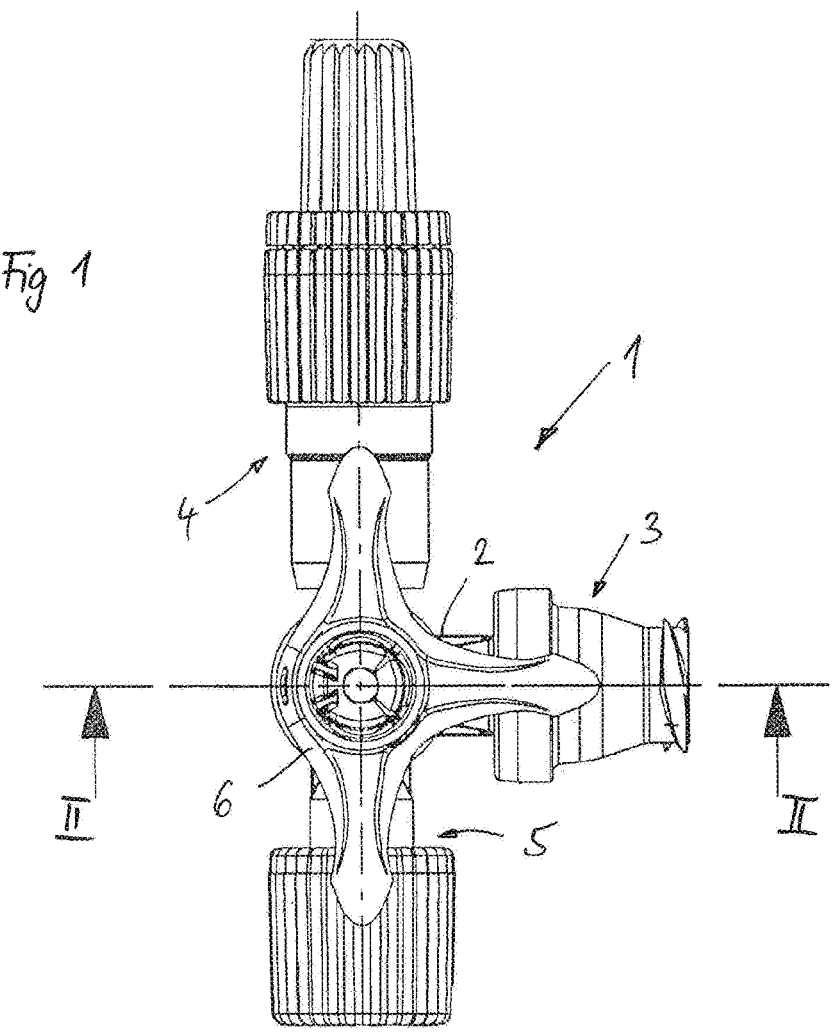

(51) Int. Cl.
  *A61M 39/26* (2006.01)
  *A61M 39/18* (2006.01)
  *F16L 37/40* (2006.01)
  *A61M 39/10* (2006.01)
  *F16K 15/18* (2006.01)

(52) U.S. Cl.
  CPC ............ *A61M 39/18* (2013.01); *A61M 39/26* (2013.01); *F16K 15/185* (2013.01); *F16L 37/40* (2013.01); *A61M 2039/1033* (2013.01); *A61M 2039/229* (2013.01); *A61M 2039/267* (2013.01); *A61M 2205/0216* (2013.01)

(58) Field of Classification Search
  CPC .................. A61M 39/10; A61M 39/18; A61M 2039/1033; A61M 2039/229; A61M 2205/0216; A61M 39/221; F16L 37/32; F16L 37/34; F16L 37/35; F16L 37/40; F16L 37/413; F16L 37/42; F16K 15/185
  See application file for complete search history.

(56) References Cited

U.S. PATENT DOCUMENTS

| | | | |
|---|---|---|---|
| 5,501,426 A * | 3/1996 | Atkinson | A61M 39/045 251/149.1 |
| 5,806,831 A * | 9/1998 | Paradis | A61M 39/02 251/149.1 |
| 5,807,348 A | 9/1998 | Zinger et al. | |
| 6,050,978 A * | 4/2000 | Orr | A61M 39/26 251/149.1 |
| 6,183,448 B1 | 2/2001 | Mayer | |
| 6,189,859 B1 * | 2/2001 | Rohrbough | A61M 39/04 251/149.1 |
| 6,206,861 B1 | 3/2001 | Mayer | |
| 6,651,956 B2 | 11/2003 | Miller | |
| 6,808,161 B1 * | 10/2004 | Hishikawa | A61M 39/045 251/149.1 |
| 7,913,716 B2 * | 3/2011 | Ostergaard | E21B 33/038 137/614.03 |
| 8,133,209 B2 * | 3/2012 | Guala | A61M 39/26 604/249 |
| 9,138,572 B2 * | 9/2015 | Zeytoonian | A61M 39/045 |
| 2002/0002351 A1 | 1/2002 | Cote, Sr. et al. | |
| 2003/0050610 A1 * | 3/2003 | Newton | A61M 39/26 604/256 |
| 2003/0153895 A1 * | 8/2003 | Leinsing | A61J 1/2089 604/403 |
| 2005/0087715 A1 * | 4/2005 | Doyle | A61M 39/045 251/149.1 |
| 2005/0148994 A1 | 7/2005 | Leinsing | |
| 2005/0256500 A1 * | 11/2005 | Fujii | A61M 39/045 604/523 |
| 2006/0111694 A1 * | 5/2006 | Fukai | A61M 39/045 604/403 |
| 2008/0067462 A1 | 3/2008 | Miller et al. | |
| 2010/0030195 A1 * | 2/2010 | Hishikawa | A61M 39/1011 604/535 |
| 2012/0089086 A1 | 4/2012 | Hokanson | |
| 2012/0211946 A1 * | 8/2012 | Halili | A61M 5/162 277/607 |
| 2014/0174578 A1 | 6/2014 | Bonnal et al. | |
| 2015/0126942 A1 * | 5/2015 | Lopez | A61M 39/10 604/256 |

FOREIGN PATENT DOCUMENTS

| | | |
|---|---|---|
| EP | 1217284 B1 | 2/2009 |
| EP | 1470352 B1 | 9/2012 |
| WO | 9924090 A1 | 5/1999 |
| WO | 03066152 A2 | 8/2003 |
| WO | 2013017698 A1 | 2/2013 |

OTHER PUBLICATIONS

Supplemental European Search Report for Application No. EP 17157260.5, dated Aug. 11, 2017, 11 pages.

* cited by examiner

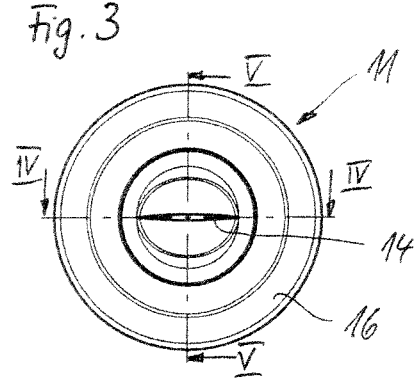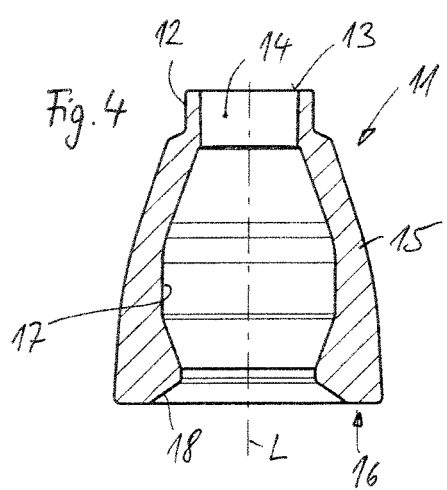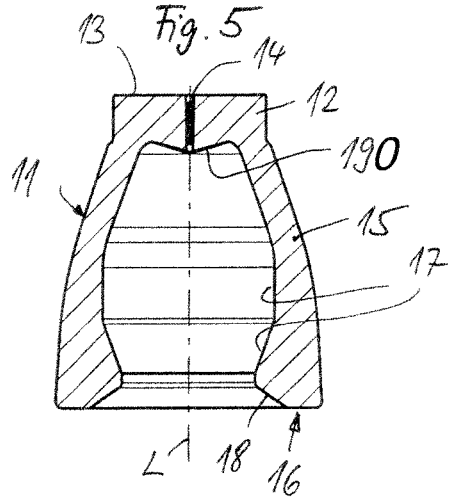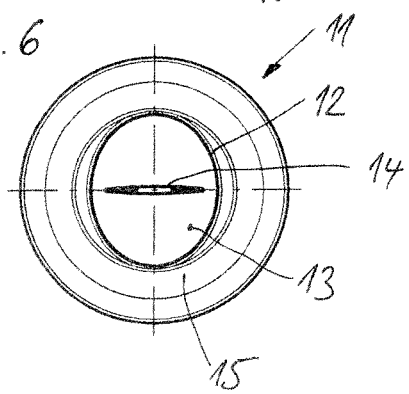

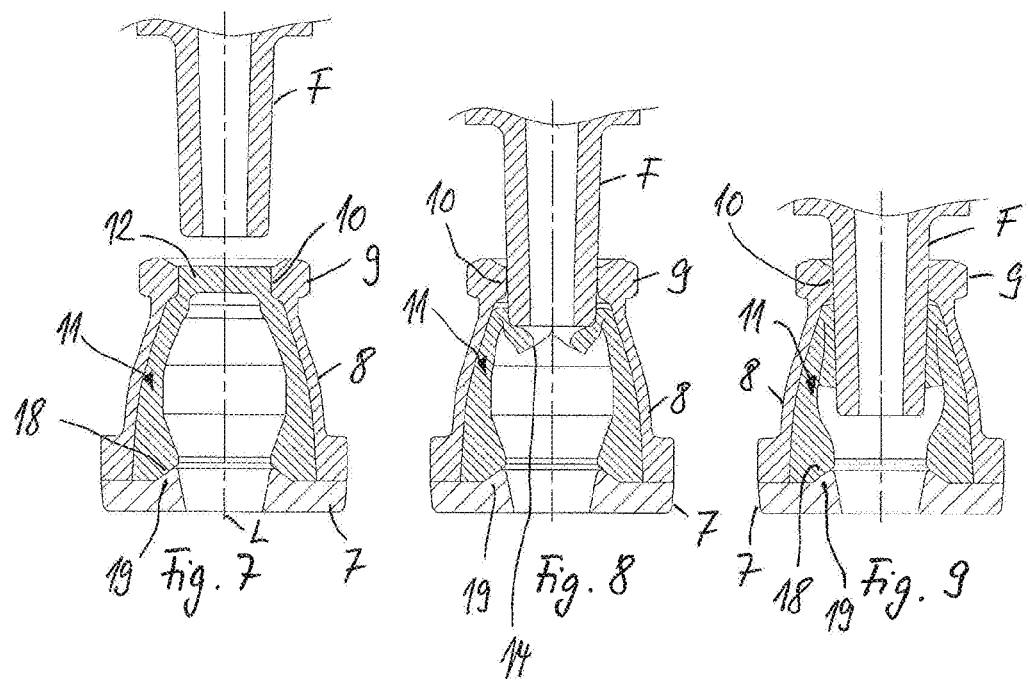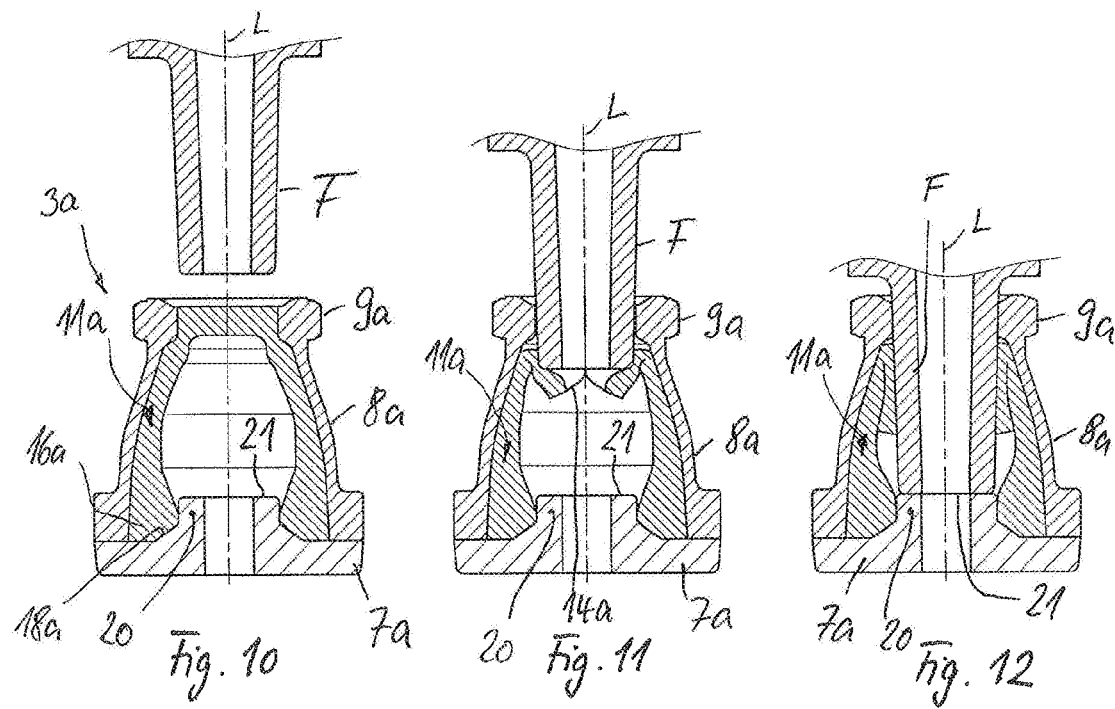

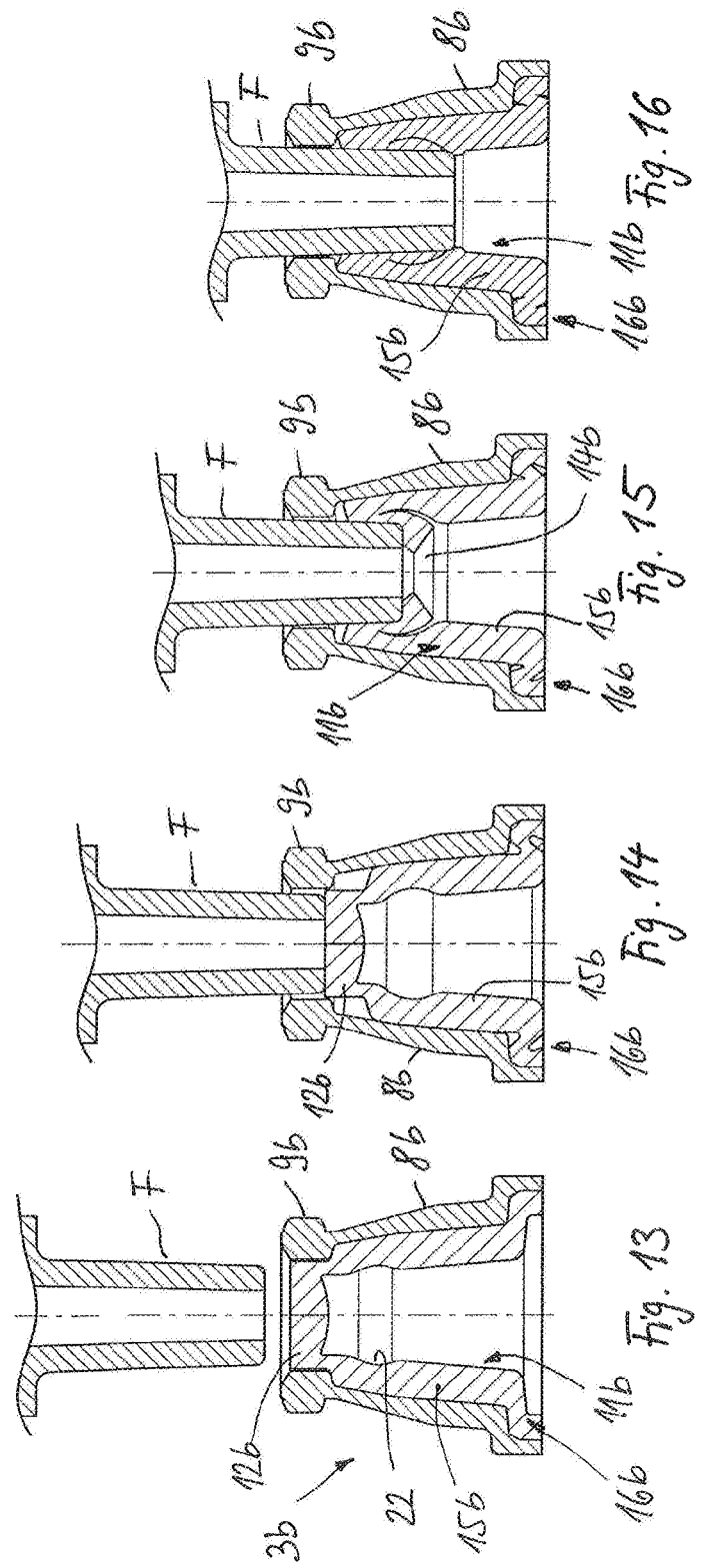

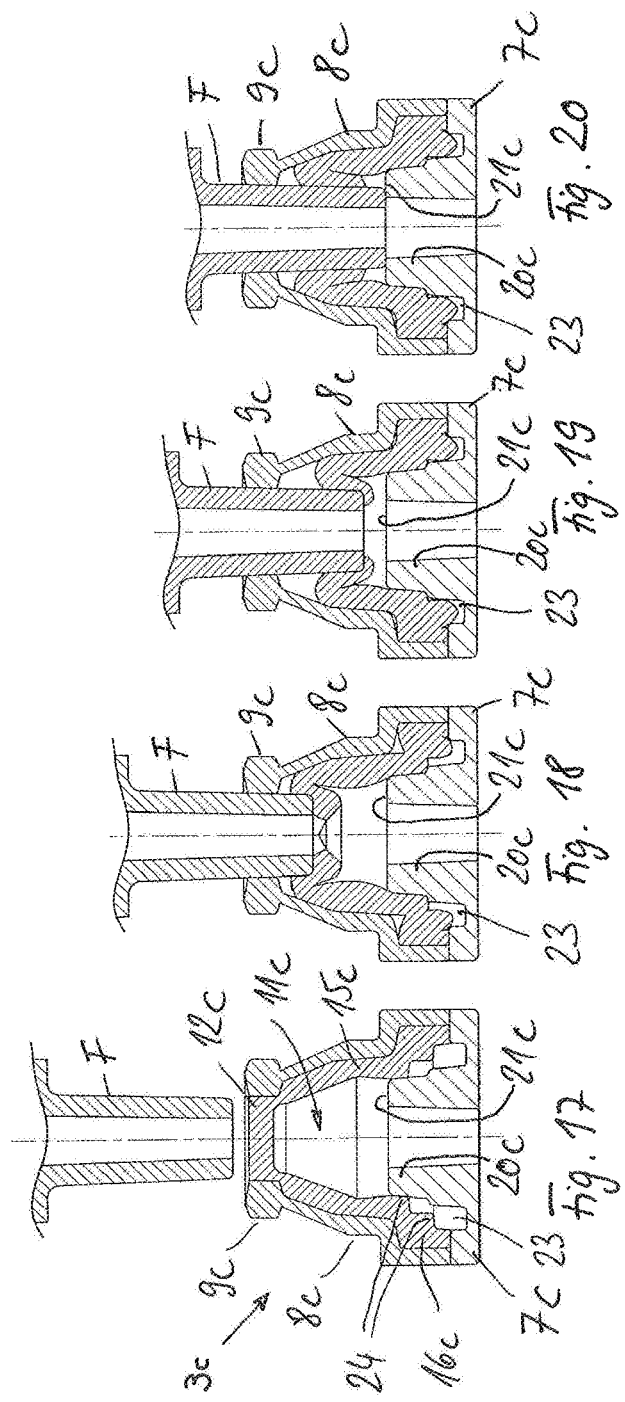

CONNECTING DEVICE FOR A MEDICAL INFUSION SYSTEM

RELATED APPLICATION(S)

This application is related to and claims the benefit of priority under 35 U.S.C. § 119 of German Application No. DE 10 2016 203 518.5, filed Mar. 3, 2016, the content of which is incorporated by reference herein in its entirety.

FIELD

The invention relates to a connecting device for a medical infusion system, having a connection piece which has a connecting profile for the connection of a functional part of the infusion system, and having a resiliently flexible, cup-like valve body which is arranged in the connection piece and has a valve casing and a cap-shaped top region which is provided with a slit arrangement, and having a dimensionally stable base portion on which a base ring of the valve casing is supported and which is firmly connected to the connection piece.

BACKGROUND

A connecting device is well known from EP 1 217 284 B1. The connecting device has a connection piece in which a valve body is integrated. The valve body seals off the connection piece in the unloaded initial state and is embodied in a cup-like and resiliently flexible manner. The valve body is produced in one piece from an elastomer material. A top region of the valve body is provided with a slit arrangement which widens in the event of elastic deformation of the valve body and thus allows throughflow through the valve body. Elastic deformation of the valve body occurs when the connection piece is connected to a further functional part of the medical infusion system, in particular an infusion syringe, a hose system or the like.

EP 1 470 352 B1 shows a further connecting device for a medical infusion system, in which an elastically deformable valve body is likewise integrated in a connection piece, said valve body being formed in a cup-like manner and having an openable slit arrangement in a cap-shaped top region.

A further connecting device is known from WO 2013/017698 A1. The known connecting device has a connection piece which is provided with Luer profiles in order to allow the connection of a functional part, provided with a complementary Luer connector, of the medical infusion system. Integrated in the connection piece, in order to seal off an opening in the connection piece, is a cup-like valve body, which is produced integrally from an elastically deformable material. The valve body expands substantially continuously from a cap-shaped top region to a base ring, with the result that the valve body has a bell shape. The valve body is provided with a slit arrangement in its top region in the same way as is the case in the valve bodies of the previously described connecting devices.

SUMMARY

It is the object of the invention to create a connecting device of the type mentioned at the beginning, which allows reliable connection and disconnection of a functional part without fluid loss or fluid contamination occurring.

This object is achieved in that, in the unloaded initial state, the valve casing has a convex internal contour which, starting from the cap-shaped top region, first of all expands in the direction of the base ring and subsequently narrows again, forming an O-like internal longitudinal section. This allows the valve body to be opened easily by elastic deformation and allows the valve body to be reset reliably into an unloaded, closed initial state. The solution according to the invention is suitable in a particularly advantageous manner for use in a connecting device in the form of a three-way stopcock. The firm connection of the dimensionally stable base portion to the connection piece can be provided by a releasable or non-releasable connection. Alternatively, the connection piece and the dimensionally stable base portion can be connected integrally together. The connection piece can be embodied as a dimensionally stable cover which is firmly connectable to the base portion and accommodates the valve body and is also fixed relative to the base portion. The valve body can be fixed by means of its base ring in the region of the dimensionally stable base portion in a force-fitting manner by clamping and/or in a cohesive manner by adhesive bonding or welding. The slit arrangement of the top region of the valve body is either embodied as a closed slit, in particular in the form of an incision, or in the manner of a partially open slot. The term "slit arrangement" accordingly includes both a closed and a partially open design.

In one configuration of the invention, a wall of the valve casing thickens from the top region to the base ring. As a result, there is elastic flexibility which reduces from the top region to the base ring. The thickening is embodied in a discontinuous and non-linear manner.

In a further configuration of the invention, a contact area of the base ring is formed at least partly in a conical manner, and the dimensionally stable base portion is formed in a complementary conical manner in order for the base ring to be supported extensively on the base portion. As a result, reliable centring and fixing of the base ring of the valve body to the dimensionally stable base portion is achieved. Therefore, in particular easier fitting of the valve body in the connection piece and on the base portion is achievable.

In a further configuration of the invention, an outer face of the cap-shaped top region is formed in a planar manner and terminates flush with a peripheral edge of the connection piece. A peripheral edge of the connection piece is in particular a chamfer of the peripheral region of the connection piece. Alternatively, the peripheral edge of the connection piece can also be understood as being an outer peripheral face of the connection piece. As a result of the planar design of the outer face, easy cleaning and disinfection of the top region and of the peripheral region of the connection piece are achievable by simple wiping or swabbing by means of a disinfectant wipe. This makes handling easier for the medical personnel. The smooth surfaces additionally prevent contamination of the outer face of the top region or of the peripheral region of the connection piece.

In a further configuration of the invention, an inwardly directed contour of the cap-shaped top region is formed in a dome-like manner. The dome-like design can be formed as a convexity or as a polygonal or conical tip. As a result, the top region is thickened, and so improved and damage-free introduction of the slit arrangement into the top region is achievable.

The object underlying the invention is also achieved in that the dimensionally stable base portion has an annular mating shoulder which projects into the base ring of the valve casing in the direction of the top region. The annular mating shoulder serves to limit projection of a tip of a functional part into the connection piece, and accordingly into the valve body, when this functional part is connected to the connection piece. As a result of the projection depth being limited, overloading of the elastic deformation of the valve body is avoided, resulting in longer durability of the valve body. In addition, high releasing forces upon disconnection of the functional part are avoided. The functional part to be connected preferably has a male Luer tip of a Luer slip or Luer lock connector, which projects into the connection piece with the valve body being elastically deformed.

In one configuration of the invention, the mating shoulder has a planar end face oriented radially with respect to a longitudinal centre axis of the connection piece. As a result, the functional part connected to the connection piece meets the mating shoulder in an extensive and abutting manner, resulting in particularly reliable and precise limiting of the penetration depth of the functional part.

In a further configuration of the invention, the base portion has an annular groove which surrounds the mating shoulder, into which some of the valve casing protrudes in the event of elastic deformation, and which forms a free annular space in the unloaded initial state of the valve body. The free space formed in this way allows the material of the valve casing to yield elastically, and so axial compression of the valve body is achievable. The axial compression additionally defines axial pretensioning, which ensures that the valve body reliably returns to its unloaded initial state again, in which the connection piece is sealed off again, following disconnection of the functional part.

In a further configuration of the invention, the annular groove has a stepped annular profile. The stepped annular profile preferably reproduces a complementary gradation of an internal contour of the base ring of the valve body, in order to define improved axial compression in the form of step-like force generation. The step-like force generation results from that fact that, in the event of axial deformation, the complementary annular steps support one another briefly up to a defined increase in force.

The object underlying the invention is also achieved in that an internal contour of the valve casing is provided, at a distance from an inner face of the top region, with a radially outwardly extended annular recess which defines in particular a flexure bearing for the valve casing in the event of elastic deformation of the valve body. The annular recess forms a radial annular free space into which the top region can protrude in the event of elastic deformation and inward buckling, while more space is available inside the valve duct for the penetration of the syringe of the solid-body part. In addition, in the event of axial compression of the valve body, this ensures annular buckling, i.e. inversion, of the top region inwards in the direction of the base ring, with the result that the slit arrangement widens and corresponding outer-face regions of the top region and of the valve casing bear extensively against a correspondingly penetrating Luer tip of the functional part. This results in a particularly good seal between the valve body and functional part. Upon disconnection and accordingly axial extraction of the Luer tip, the inwardly inverted portions of the valve body are perforce entrained outwards again, such that the valve body returns to its initial state again, in which it seals off the connection piece.

In one configuration of the invention, the base ring has an annular shoulder with a thinned wall region which is formed such that, in the event of axial compressive stress being applied to the valve body from the top region, the valve casing is axially inverted in the region of the base ring. This results in clearly defined axial deformation of the valve body, which allows the valve body to return reliably into an unloaded initial state, without the risk of a permanent kink and accordingly failure of the valve body arising.

In a further configuration of the invention, the valve casing is formed in a rotationally symmetrical manner and the top region is formed in a rotationally asymmetrical manner, in particular in an oval manner. Advantageously, an opening region of the connection piece, which, with its peripheral region, surrounds the top region of the valve body in the unloaded initial state thereof, is also formed in a complementary oval manner.

In a further configuration of the invention, the slit arrangement has been introduced along a transverse extent of the top region. This allows reliable opening and closing of the slit arrangement in the event of corresponding elastic deformation.

The invention also relates to a valve body for a connecting device as described above, wherein the valve body is formed in a resiliently flexible and cup-like manner and is provided with a top region and a valve casing as are embodied on the basis of the above-described features.

BRIEF DESCRIPTION OF THE DRAWING FIGURES

Further features and advantages of the invention can be gathered from the claims and from the following description of preferred exemplary embodiments of the invention, which are illustrated by way of the drawings.

Figure 2:
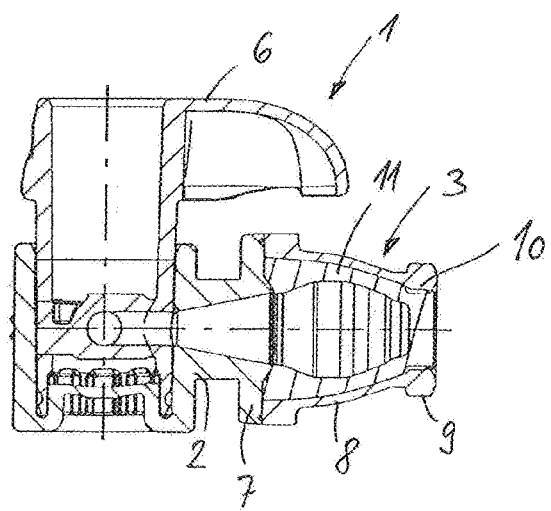

FIG. 1 shows a plan view of an embodiment of a connecting device according to the invention in the form of a three-way stopcock, FIG. 2 shows a section through the connecting device according to FIG. 1 along the section line II-II in FIG. 1, FIG. 3 shows a bottom view of a valve body of the connecting device according to FIG. 2, FIG. 4 shows a longitudinal section through the valve body according to FIG. 3 along the section line IV-IV in FIG. 3, FIG. 5 shows a further longitudinal section through the valve body along the section line V-V in FIG. 3, FIG. 6 shows a plan view of the valve body according to FIGS. 3 to 5, FIGS. 7 to 9 show sectional illustrations of different steps in the connection of a functional part to a connection piece of the connecting device according to FIG. 2, FIGS. 10 to 12 show different functional steps in the further connection of a functional part to a connection piece of another embodiment of a connecting device according to the invention that is similar to FIG. 2, FIGS. 13 to 16 show sectional illustrations of different functional steps in the connection of a functional part to a connection piece of a further embodiment of a connecting device according to the invention, and FIGS. 17 to 20 show sectional illustrations of functional steps in the connection of a functional part to a connection piece of a further embodiment of a connecting device according to the invention.

DETAILED DESCRIPTION OF EMBODIMENTS

A connecting device 1 for a medical infusion system is formed as a three-way stopcock. The connecting device 1 has a housing 2 in which an actuator 6 is mounted in a rotatable manner. A total of three connecting ducts are provided in the housing 2, said connecting ducts being shut off or connected together, depending on the position of the actuator 6. One connecting duct of the housing 2 leads to a connection piece 3. A further connecting duct, arranged at right angles thereto, leads to a connection region 4 and, opposite thereto, a third connecting duct leads to a connection region 5. One of the two connection regions 4, 5 is intended for the connection of a patient line. The other connection region 4, 5 serves to attach a connecting line to a fluid container.

The connection piece 3 is provided for the temporary connection of a functional part of the infusion system, in particular a syringe, in order to feed additional medicines or the like to the patient line. The connection piece 3 is explained in more detail by way of FIGS. 2 to 9.

The connection piece 3 has a dimensionally stable cover 8 which is firmly connected, on its end side facing the housing 2, to a dimensionally stable base portion 7 of the housing 2. The cover 8 is formed in a sleeve-like manner and has, on its side facing the base portion 7, a thickened peripheral region which is firmly connected to the base portion 7, in the present case by welding. The base portion 7 is embodied in a plate-like manner and projects radially outwards relative to a longitudinal centre axis L of the connection piece 3. The base portion surrounds a duct portion that narrows conically with respect to an interior of the housing 2.

The cover 8 is provided, in its end region remote from the base portion 7, with a passage 10 which is able to be closed by a valve body 11 that is described in more detail in the following text. The passage 10 is enclosed by a thickened peripheral region which is provided with connecting profiles 9 in the form of Luer lock profiles.

The valve body 11 is formed in a cup-like or bell-like manner and produced in one piece from a resiliently flexible material, in the present case from an elastomer or a thermoplastic elastomer. Particularly advantageously, the valve body 11 is produced from silicone. The valve body 11 has an external contour which, in the unloaded initial state, bears in a flush and extensive manner against the internal contour of the cover 8 over the entire height of the cover 8. The valve body 11 is provided with a cap-shaped top region 12 which has a rotationally asymmetrical, in the present case oval, area (see in particular FIGS. 3 and 6). The top region 12 is adjoined by a valve casing 15 which is provided in its lower end region with a base ring 16. The top region 12 is provided with a slit arrangement 14. A surface 13 of the top region 12 is formed in a smooth and planar manner. It is clear from FIG. 7 that the surface of the top region 12 terminates flush with a peripheral edge of the passage 10 in the unloaded initial state of the valve body 11 in the cover 8. An oblique chamfer extends outwards from this peripheral edge of the passage 10 as far as an end face of the peripheral region, defining the passage 10, of the cover 8. Accordingly, in the unloaded initial state of the valve body 11, the end face of the peripheral region of the cover 8, including the surface of the top region 12 of the valve body 11, can be cleaned and disinfected easily by medical personnel by means of a disinfectant wipe or the like.

The valve casing 15 of the valve body 11 is embodied in a rotationally symmetrical manner relative to the longitudinal centre axis L and has a wall which thickens from the top region 12 to the base region 16. The thickening occurs discontinuously and non-linearly, as can be seen from the two visible edges illustrated. The edges are annularly encircling. In this case, the valve casing 15 has a first wall portion that adjoins the top region 12, widens in a frustoconical manner and has a constant thickness. This first wall portion is adjoined, in the direction of the base ring 16, by a second wall portion, the inner wall of which extends cylindrically and coaxially with the longitudinal centre axis L, and the outer wall of which extends in a manner bulging further outwards in the direction of the base ring 16. This central wall portion is adjoined by the base-side wall portion, which comprises the base ring 16. In this region, the inner wall extends in a narrowed manner from the cylindrical central region to the base portion, resulting in an inner wall portion that tapers conically downwards.

The inner wall widens conically again towards an end side of the base ring 16, forming a contact area 18. Accordingly, an egg-like or O-like internal contour 17 arises over the height of the valve casing 15 (FIGS. 4 and 5).

An inner face, directed into the interior of the valve casing 15, of the top region 12 is formed as a dome-like contour 190, as can be gathered from FIG. 5.

The passage 10 in the cover 8 can be formed in a rotationally symmetrical or rotationally asymmetrical manner. In the case of a rotationally asymmetrical top region 12, the passage 10 is preferably also formed in a complementary rotationally asymmetrical manner.

As can be seen in FIGS. 2 and 7 to 9, the conical contact area 18 of the base ring 16 of the valve body 11 is assigned a complementary conical supporting face 19 in the region of the base portion 7, with the result that the valve body 11 is supported extensively on the base portion 7 over its entire radial width in the region of the base ring 16.

The slit arrangement 14 is oriented transversely to a longitudinal extent of the oval top region 12, as can be seen from FIGS. 4 to 6. The slit arrangement 14 extends centrally along the longitudinal centre axis L through the top region 12.

As soon as a tip of a functional part F (see FIGS. 7 to 9) to be connected to the connection piece 3 is now guided up to the connection piece 3 from the outside, the tip comes into contact with the outer face of the top region 12 extensively and pushes the top region 12 into the interior of the cover 8. In the process, the slit arrangement 14 widens and the elastically deformed portions of the top region 12 bear against the outside of the tip upon further penetration of the tip of the functional part F. Upon disconnection and resultant removal of the tip towards the outside, the top region 12 returns to the initial state according to FIG. 7 again.

The connecting device according to FIGS. 10 to 12 corresponds substantially to the above-described connecting device according to FIGS. 1 to 9. Functionally identical parts and portions are provided with the same reference signs with addition of the letter a. In order to avoid repetitions, reference is made to the disclosure for the embodiment according to FIGS. 1 to 9. The connection piece 3a corresponds substantially to the connection piece 3 of the connecting device according to FIGS. 1 to 9. The cover 8a and the valve body 11a are formed identically to the cover 8 and the valve body 11 according to FIGS. 1 to 9. The cover 8a can in particular have been connected cohesively to the base portion 7a by welding. Particularly advantageously, the cover 8a is connected releasably to the base portion 7a of the housing, in particular by way of a screw connection. This makes it possible to easily exchange the valve body 11a.

The cover 8 and the covers 8b and 8c, described below, of the embodiments according to FIGS. 13 to 20 can also—depending on the embodiment—be connected releasably or non-releasably to the respective base portion 7, 7b, 7c. The releasable connection takes place advantageously by way of a screw connection.

An essential difference of the base portion 7a from the base portion 7 is that the base portion 7a is provided, next to the conical supporting face 18a for the base ring 16a of the valve body 11a, with an integrally formed, annular mating shoulder 20 which projects in a cylindrical manner into the internal contour of the valve body 11a towards the top region of the valve body 11a. The mating shoulder 20 is provided with a planar end face that extends radially relative to the longitudinal centre axis L. The mating shoulder 20 serves as a stop for the tip of the functional part F, such that the penetration depth of the tip of the functional part into the connection piece 3a is limited. The tip of the functional part F is provided with a complementary planar end face which is extended radially with respect to the longitudinal centre axis L in the connected state of the functional part and accordingly rests in an extensive and flush manner on the end face 21 of the mating shoulder 20 (FIG. 12).

The fact that the mating shoulder 20 limits the penetration depth of the tip ensures that the valve body 11a is not deformed too greatly, which could result in damage to the valve body 11a. Moreover, the limiting of the penetration depth of the tip ensures that the tip does not become wedged in the region of the passage of the connection piece 3a, and so the functional part, including the tip, can be disconnected without great application of force.

The valve device according to FIGS. 13 to 16 has a connection piece 3b which is fastened to a base portion of the housing in a manner that is not illustrated in more detail. Functionally identical parts and portions of the connecting device and of the connection piece 3b are provided with the same reference signs with addition of the letter b. In this embodiment, too, reference is made to the above-described embodiments in order to avoid repetitions with regard to the functionally identical parts and portions. The differences of the connection piece 3b will be dealt with in the following text.

The valve body 11b is formed as a one-piece elastomer body in the same way as the valve bodies 11 and 11a according to the above-described embodiments. However, the valve body 11b has a different shape and a different deformation function. The cup-like or bell-like valve body 11b is provided with a top region 12b which is adjoined by a valve casing 15b that transitions into a base ring 16b. The top region 12b is provided with a slit arrangement 14b. The valve casing 15b is provided, at a distance below the top region 12b, in the region of its internal contour, with an annular recess 22 which forms an annular flexure bearing in the valve casing. In addition, at the transition of the valve casing 15b to the base ring 16b, a radially outwardly extended annular step is provided, the wall thickness of which is less than the wall thickness of the valve casing 15b. As a result, a further annular flexure bearing is formed. Finally, in the direction of the top region 12b, the valve casing 15b transitions into the top region 12b likewise with a narrower annular casing region. In this region, too, an annular flexure bearing is accordingly perforce formed. Accordingly, folds or inversions arise in the region of the described flexure bearings as soon as an axial force is exerted on the valve body 11b from the outside. In this case, the flexure bearings are coordinated with one another such that, upon axial compressive stress being applied to the top region 12b from the outside by a tip of a functional part F, first of all the top region 12b and the valve casing 15b are pushed axially inwards in a substantially non-deformed manner, with the flexure bearing being deformed in the region of the base ring 16b (FIG. 14). In the process, a corresponding portion of the valve casing 15b merely comes into abutment against an end face of the base portion of the housing in the indicated manner, such that the valve casing 15b cannot be pushed axially inwards further. The deformed flexure bearing in the region of the base ring 16b perforce exerts an axial opposing force on the valve body 15b, said opposing force causing the valve body 11b to return elastically into the unloaded initial state according to FIG. 13 after removal of the compressive stress. If the tip of the functional part F now penetrates further inwards into the connection piece 3b—as can be seen in FIGS. 14 to 16—the flexure bearing now collapses in the region of the top region 12b, wherein the narrower annular step in the top region 12b is elastically deformed. An inner side of the top region 12b perforce bears against the internal contour of the valve casing 15b in the region of the recess 22 on account of the expansion of the supporting arrangement 14b, with the result that the top region 12b is pushed inwards and downwards. The valve casing 15b is displaced against the inner wall of the cover 8b, with the result that the valve casing, including the top region 12b, bears in a substantially extensive manner against the external contour of the tip F.

When the tip F is extracted, the valve body 15b returns to the unloaded initial state according to FIG. 13 again.

The connection piece 3c according to FIGS. 17 to 20 is likewise provided in a connecting device as illustrated in FIGS. 1 and 2. Functionally identical parts and portions are provided with the same reference signs with addition of the letter c. In order to avoid repetitions, reference is additionally made to the disclosure of the above-described embodiments. The connection piece 3c, too, has a cover 8c which is firmly connected in a releasable or non-releasable manner to a base portion 7c of the housing. The cover 8c has, in its end region remote from the base portion 7c, a passage, which is enclosed by a peripheral region that is provided with connecting profiles 9c, in the present case in the form of Luer lock profiles. Integrated in the connection piece 3c is a valve body 11c which is in the form of a one-piece elastomer component. The valve body 11c has a top region 12c which closes the passage through the cover 8c and is provided with a slit arrangement. The base portion 7c is provided with a mating shoulder 20c for limiting the penetration depth of the tip of a functional part F embodied as a male Luer lock part. The mating shoulder 20c has an end face 21c on which the end face of the tip bears in the connected state. The valve body 11c is provided with an annular flexure bearing at the transition of the valve casing 15c to the base ring 16c. The base ring 16c is provided, in the region of its inner side, with two annular steps 24, which are formed such that, in the event of axial compressive stress being applied by the tip of the functional part F, the valve casing 15c can kink annularly and accordingly be elastically deformed both in the region of the base ring 16c and at the transition between the top region 12c and valve body 15c. In order not to prevent the inversion or kinking inwards in the region of the base ring 16c, a stepped annular groove 23 is provided at the transition between the mating shoulder 20c and a radial annular shoulder of the base portion 7c, said annular groove 23 forming an annular free space. The stepped annular groove 23 extends axially into the base portion 7c and has, at a distance above its bottom, an annular ledge (not designated further), on which a first annular step 24 of the valve casing 15c axially impinges in the event of an axial deformation of the valve body 11c. Upon further axial deformation, the valve body 11c deforms further at the transition from the valve casing 15c to the base ring 16c, with the result that the displaced material of the valve casing 15c protrudes into the free space 23, as can be seen from FIGS. 19 and 20. As a result of the widening of the slit arrangement, the tip of the functional part F can impinge on the end face 21c of the mating shoulder 20c. The top region 12c bears against the outside of the tip, as can be seen in FIG. 20. Upon disconnection of the functional part F, the tip is removed from the passage again, with the result that the valve body 11c returns to the unloaded initial state according to FIG. 17 again.

The invention claimed is:

1. A connecting device for a medical infusion system, the connecting device having a connection piece, the connection piece having a connecting profile for connection of a functional part of the infusion system, the connection piece also having a resiliently flexible, cup-like valve body arranged in the connection piece, the valve body having a valve casing and a cap-shaped top region which is provided with a slit arrangement, the connection piece further comprising a dimensionally stable base portion on which a base ring of the valve casing is supported, the base portion firmly connected to the base ring, wherein, in an unloaded initial state, the valve casing has a convex internal contour which, starting from the cap-shaped top region, first of all expands in a direction of the base ring and subsequently narrows again, the valve casing comprising a first wall portion having a constant thickness, the first wall portion adjoining the cap-shaped top region and widening in a frustoconical manner, the first wall portion also adjoining a central wall portion in a direction toward the base portion, the central wall portion comprising a first inner wall that extends cylindrically and coaxially with respect to a longitudinal center axis of the connection piece, the central wall portion also comprising a first outer wall that is curved and expands radially outwardly and away from the longitudinal center axis as the first outer wall extends toward the base portion, the central wall portion adjoined to a base-side wall portion that comprises the base ring, the base-side wall portion comprising a second inner wall adjacent to and contiguous with the first inner wall, the second inner wall having a first portion expanding radially outwardly and away from the longitudinal center axis and widening conically as the second inner wall extends toward an end side of the base ring to form a conical contact area on the base ring.

2. The connecting device according to claim 1, wherein the valve casing has a wall thickness that thickens from the cap-shaped top region to the base ring.

3. The connecting device according to claim 1, wherein the base portion is formed in a complementary conical manner with the conical contact area of the base ring in order for the base ring to be supported extensively on the base portion.

4. The connecting device according to claim 1, wherein an outer face of the cap-shaped top region is formed in a planar manner and terminates flush with a peripheral edge of the connection piece.

5. The connecting device according to claim 1, wherein an inwardly directed contour of the cap-shaped top region is formed in a dome-like manner.

6. The connecting device according to claim 1, wherein the base portion has an annular mating shoulder which projects into the base ring of the valve casing in a direction of the cap-shaped top region.

7. The connecting device according to claim 6, wherein the mating shoulder has a planar end face oriented radially with respect to the longitudinal center axis of the connection piece.

8. The connecting device according to claim 1, wherein the valve casing is formed in a rotationally symmetrical manner and the cap-shaped top region is formed in a rotationally asymmetrical manner.

9. The connecting device according to claim 8, wherein the slit arrangement is introduced along a transverse extent of the cap-shaped top region.

10. A valve body for a connecting device, said valve body being formed in a resiliently flexible and cup-like manner and being provided with a cap-shaped top region and a valve casing in accordance with claim 1.

11. The connective device according to claim 1, wherein the second inner wall comprises a second portion adjacent to and contiguous with the first inner wall, the second portion tapering radially inwardly and toward the longitudinal axis as it extends from the first inner wall toward the conical contact area.

* * * * *